(12) United States Patent
Meswania et al.

(10) Patent No.: US 8,021,433 B2
(45) Date of Patent: *Sep. 20, 2011

(54) MODULAR LONG BONE PROSTHESIS

(75) Inventors: Jay Meswania, Hertfordshire (GB); Paul Unwin, Hertfordshire (GB)

(73) Assignee: Stanmore Implants Worldwide Limited, Stanmore, Middlesex (GB)

( * ) Notice: Subject to any disclaimer, the term of this patent is extended or adjusted under 35 U.S.C. 154(b) by 779 days.

This patent is subject to a terminal disclaimer.

(21) Appl. No.: 11/981,394

(22) Filed: Oct. 31, 2007

(65) Prior Publication Data

US 2008/0133024 A1 Jun. 5, 2008

Related U.S. Application Data

(63) Continuation-in-part of application No. 11/433,953, filed on May 15, 2006, now Pat. No. 7,662,189, which is a continuation of application No. 10/450,559, filed as application No. PCT/GB01/05456 on Dec. 7, 2001, now Pat. No. 7,044,976.

(30) Foreign Application Priority Data

Dec. 15, 2000 (GB) .................................. 0030643.1

(51) Int. Cl.
*A61F 2/32* (2006.01)
*A61F 2/28* (2006.01)

(52) U.S. Cl. ................. 623/22.42; 623/22.11; 623/22.4; 623/16.11

(58) Field of Classification Search .... 623/22.41–22.46, 623/20.15, 20.34, 20.36, 23.18, 23.21, 23.26, 623/23.44, 22.11, 22.4, 16.11
See application file for complete search history.

(56) References Cited

U.S. PATENT DOCUMENTS

| | | | | |
|---|---|---|---|---|
| 4,963,155 A * | 10/1990 | Lazzeri et al. | ............. | 623/22.42 |
| 5,201,767 A * | 4/1993 | Caldarise et al. | ........... | 623/23.35 |
| 6,613,092 B1 * | 9/2003 | Kana et al. | ................ | 623/20.15 |
| 7,044,976 B2 * | 5/2006 | Meswania | ................ | 623/22.45 |
| 7,297,166 B2 * | 11/2007 | Dwyer et al. | ............... | 623/22.12 |
| 7,582,092 B2 * | 9/2009 | Jones et al. | .................. | 606/102 |
| 7,662,189 B2 * | 2/2010 | Meswania | ................ | 623/22.45 |

* cited by examiner

*Primary Examiner* — Pedro Philogene
(74) *Attorney, Agent, or Firm* — Galgano & Associates, PLLC; Thomas M. Galgano; Jessica G. Bower (57) ABSTRACT

A prosthesis for partial replacement of a long bone in humans or animals, the prosthesis including: a proximal or distal end component forming one component of a prosthetic joint; a shaft on or assembled with the distal or proximal end component in use; a stem for engagement in a resected bone; and an initially separate collar assembled to the shaft or an extension thereof in use, the collar being dimensioned to abut the resected end face of the bone into which the prosthesis is to be fitted, wherein the end face of the collar facing the resected face of the bone is sized and shaped to correspond to the resected end face of the bone.

68 Claims, 11 Drawing Sheets

MODULAR LONG BONE PROSTHESIS

CROSS-REFERENCE TO RELATED APPLICATION

This application is a continuation-in-part of application Ser. No. 11/433,953 filed May 15, 2006, which is a continuation of application Ser. No. 10/450,559, filed Jun. 12, 2003, now U.S. Pat. No. 7,044,976.

FIELD OF THE INVENTION

This invention relates to prostheses for partial replacement of a long bone in human or animal bodies.

BACKGROUND TO THE INVENTION

In the case where limbs are badly damaged or large amounts of bone must be surgically removed, e.g. in the case of treatment of bone cancer, there is a need for prostheses which replace a large part of the natural bone and which can be assembled by the surgeon to meet a wide range of conditions. The present invention provides a modular system and components thereof for constructing effectively customised prostheses to meet a range of such surgical requirements. Typical requirements may be, for example, to replace the proximal or distal femur. Existing modular prostheses for the purpose such as, for example, those in U.S. Pat. No. 4,623,349, U.S. Pat. No. 4,963,155 and U.S. Pat. No. 6,048,365 generally allow customisation but generally do not accommodate for significant differences between patients and do not allow for effective, cost-effective and efficient tailoring of the prosthesis to the needs of a patient.

SUMMARY OF THE INVENTION

According to one aspect of the present invention there is provided a prosthesis for partial replacement of a long bone in humans or animals, said prosthesis comprising a proximal or distal end component forming one component of a prosthetic joint, a shaft assembled with the distal or proximal end and a stem for engagement in a resected bone, including a collar which may be assembled to the shaft or extension thereof, the collar being dimensioned to abut the resected face of bone into which the prosthesis is to be fitted, wherein the end face of the collar facing the resected face of the bone is sized and shaped to correspond to the resected end face of the bone.

Preferably the collar has a portion, proximate the resected face in use, having a surface treatment adapted to encourage bone growth thereover. Suitably that portion of the collar is adapted to taper towards the resected face.

It is very important that the end of the prosthesis that abuts the resected bone of the patient is sized and shaped to approximate the resected bone. In the femur the proximal and distal segments of the bone are generally ovoid (distally with the greater dimension being medial to lateral, proximally with the greater dimension being anterior to posterior). The central section of bone is generally round. Furthermore there is significant variation in the overall dimensions of the bone between gracial female femorae and the largest robust male femorae.

The prosthesis end should not be undersized since in a weight bearing environment the prosthesis shaft may then unduly stress the bone and in certain situations may even telescope into it. Conversely it is important that the abutment end not be oversized relative to the bone since the soft tissues—muscles, tendons and ligaments—of the limb should suitably be substantially unhindered at the interface between the prosthesis and the bone to allow those soft tissues to glide freely back and forth over the bone surface and not rubbing against a raised step/shoulder at the interface leading to wear and/or tissue inflammation. By designing a separate collar defining the end face of the prosthesis that abuts the resected end face of the bone, the surgeon can be provided with a cost effective and efficient kit having multiple different collars to select amongst them the one that best suits the dimensional requirements of a given patient addressing the above problems. Furthermore, by optimally matching the abutment end of the prosthesis to the resected bone of the patient this helps to optimise osseointegration of that part of the prosthesis with the bone when that part is treated for osseointegration and thereby significantly reduces risk of aseptic loosening.

Preferably the shaft, stem and the distal or proximal end components are connected by male and female tapers, each male taper including a projection which extends longitudinally of the prosthesis but is offset from its axis and engages in a corresponding recess in the female taper. The projection maintains adjacent components in the desired angular relationship. Advantageously a cross-hole is provided for access transversely to the region of the end of the male taper by a disassembly tool.

In the case of proximal femoral replacement prostheses, the prosthesis preferably includes a trochanter replacement component assembled with a shaft and stem, the trochanter replacement component being shaped to correspond approximately with an anatomical trochanter and including a femoral neck for receiving a femoral ball and a generally flat face opposite the femoral neck for connection to residual bone or soft tissue.

According to another aspect of the invention there is provided a collar for a prosthesis for partial replacement of a long bone in humans or animals, said prosthesis comprising: a proximal or distal end component forming one component of a prosthetic joint; a shaft on or assembled with the distal or proximal end component, a stem for engagement in a resected bone; and an initially separate collar assembled to the shaft or an extension thereof in use, the collar being dimensioned to abut the resected end face of the bone into which the prosthesis is to be fitted, wherein the end face of the collar facing the resected face of the bone is sized and shaped to correspond to the resected end face of the bone.

Preferably the end face of the collar facing the resected end face of the bone is substantially circular cylindrical or ovoid cylindrical and has an outside diameter that is selected to correspond substantially to the outside diameter of the resected end face of the bone. Preferably the end face of the collar terminates inboard of the external dimension of the resected end face of the bone.

Preferably at least a portion of the collar has a surface treatment designed to encourage bone growth. Said portion of the collar may be formed with an externally stippled surface and/or coated with hydroxyapatite or other bone growth promoting material.

Preferably at least a portion of the collar is adapted to taper towards the resected end face of the bone. Preferably the collar has at least one lug or ear which is adapted to co-operatively engage with a corresponding at least one recess on said shaft of the prosthesis to counter relative rotation therebetween.

According to a further aspect of the invention there is provided a kit for a prosthesis for partial replacement of a long bone in humans or animals, said prosthesis comprising: a proximal or distal end component forming one component of a prosthetic joint; a shaft on or assembled with the distal or proximal end component; a stem for engagement in a resected bone; and an initially separate collar assembled to the shaft or an extension thereof in use, the collar being dimensioned to abut the resected end face of the bone into which the prosthesis is to be fitted, the kit comprising two or more said collars of different sizes and/or shapes.

The kit preferably comprises a greater number of collars than number of stems. The kit may comprise only one stem and a plurality of differing collars. Preferably the kit comprises at least one collar that is substantially circular cylindrical and one that is ovoid cylindrical. Preferably the kit comprises at least one collar that is surface treated for osseointegration and one that is not.

BRIEF DESCRIPTION OF THE DRAWINGS

Detailed features of prostheses in accordance with the invention will become apparent from the accompanying drawings, in which:

FIGS. 8A to 8C show side elevation views of three variants of collar having differing shapes—distally tapered, untapered and proximally tapered;

DETAILED DESCRIPTION OF THE PREFERRED EMBODIMENTS

Figure 1:
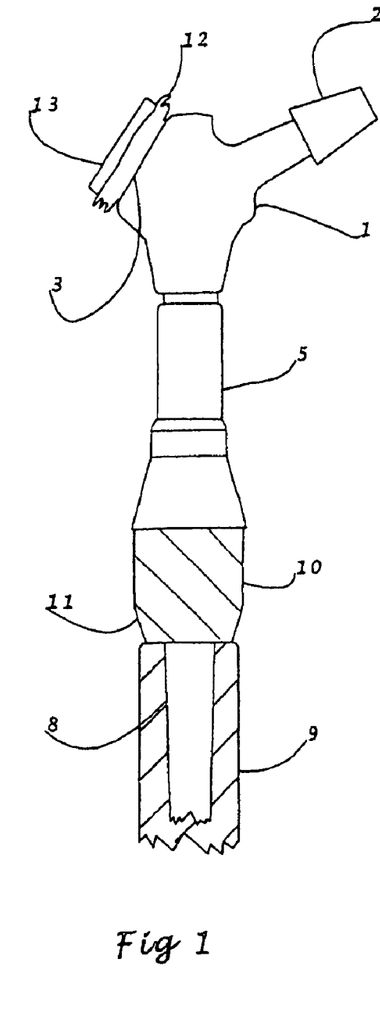
FIG. 1 is a side elevation of assembled components of a proximal femoral prosthesis.

Referring firstly to FIG. 1, this drawing shows diagrammatically an assembled, proximal femoral prosthesis comprising a trochanter component 1 having a femoral neck 2, which is tapered to receive a femoral ball in a conventional fashion. The trochanter component is shown in more detail in the views shown in FIG. 3 and it may be seen that it corresponds roughly to the anatomical shape and has a generally flat face 3 for attachment to any residual bone or to soft tissues. The trochanter component 1 has an internal female taper, best seen in FIG. 3, and is assembled onto a male taper carried by a shaft 5. The detailed construction of shaft 5 are apparent from the views in FIG. 4 and it will be seen that shaft 5 has a male taper 33 at one end for engagement into the female taper of the trochanter component 1 and at its other end has a female taper 7 for engagement with one end of a stem 8 (shown in more detail in FIG. 5).

Stem 8 is fitted into a resected femur 9 either by press-fit or by using bone cement. Surrounding the distal end of the shaft 5, is a collar 10 which is shown in more detail in FIG. 6. Collar 10 has a distal lower end 11 which abuts cancellous bone forming the face of resected bone 9. The dimensions of collar 10 are selected so that the end face of collar 10 approximates to the dimensions of the resected end face of the resected bone. As illustrated it terminates in board of the external dimension of the bone 9, ie is somewhat smaller in outside diameter than the outside diameter of the resected end face of the bone. In this first embodiment the collar 10 is formed on its external surface with stipples and coated with a bone growth stimulating material such as hydroxyapatite. These measures encourage cancellous bone to grow over the surface of collar 10 and help to more firmly lock the prosthesis into the residual resected bone 9.

It is often possible when removing damaged bone or tumour to retain the residual portion 12 of the trochanter. This residual piece of bone may have ligaments or other soft tissue attached to it and it is useful to use this to assist in stabilising the trochanter replacement component. The residual bone 12 can be attached to the trochanter component by clamping a plate 13 to the face 3 of the trochanter component.

Figure 2:
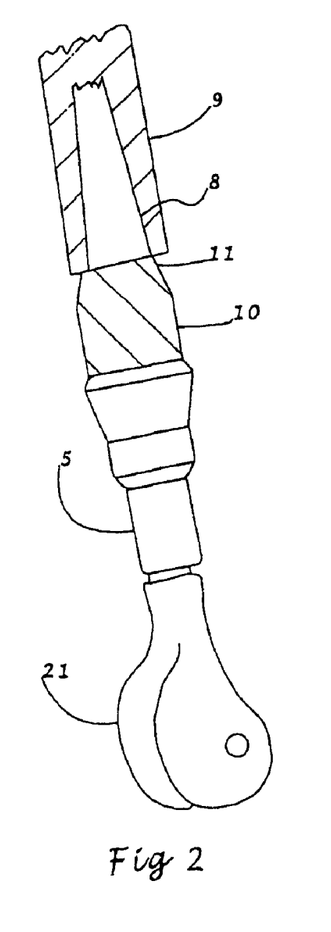
FIG. 2 is a side elevation of a distal femoral prosthesis in accordance with the invention.

FIG. 2 shows a view of an assembled distal prosthesis comprising a condylar head component 21 forming one part of the knee joint which is connected to a shaft 5 in an analogous way to the way in which the trochanter component 1 is connected to the shaft 5 in FIG. 1. Similarly, shaft 5 is connected to stem 8 in a similar way to that previously described in connection with FIG. 1 and collar 10 is slid over the tapered lower portion of shaft member 5 just as described above in connection with FIG. 1 and has a distal tapered portion 11 which abuts the resected face of the femur 9. In a similar way, this encourages bone growth over the surface of the collar 10.

Figure 3A:
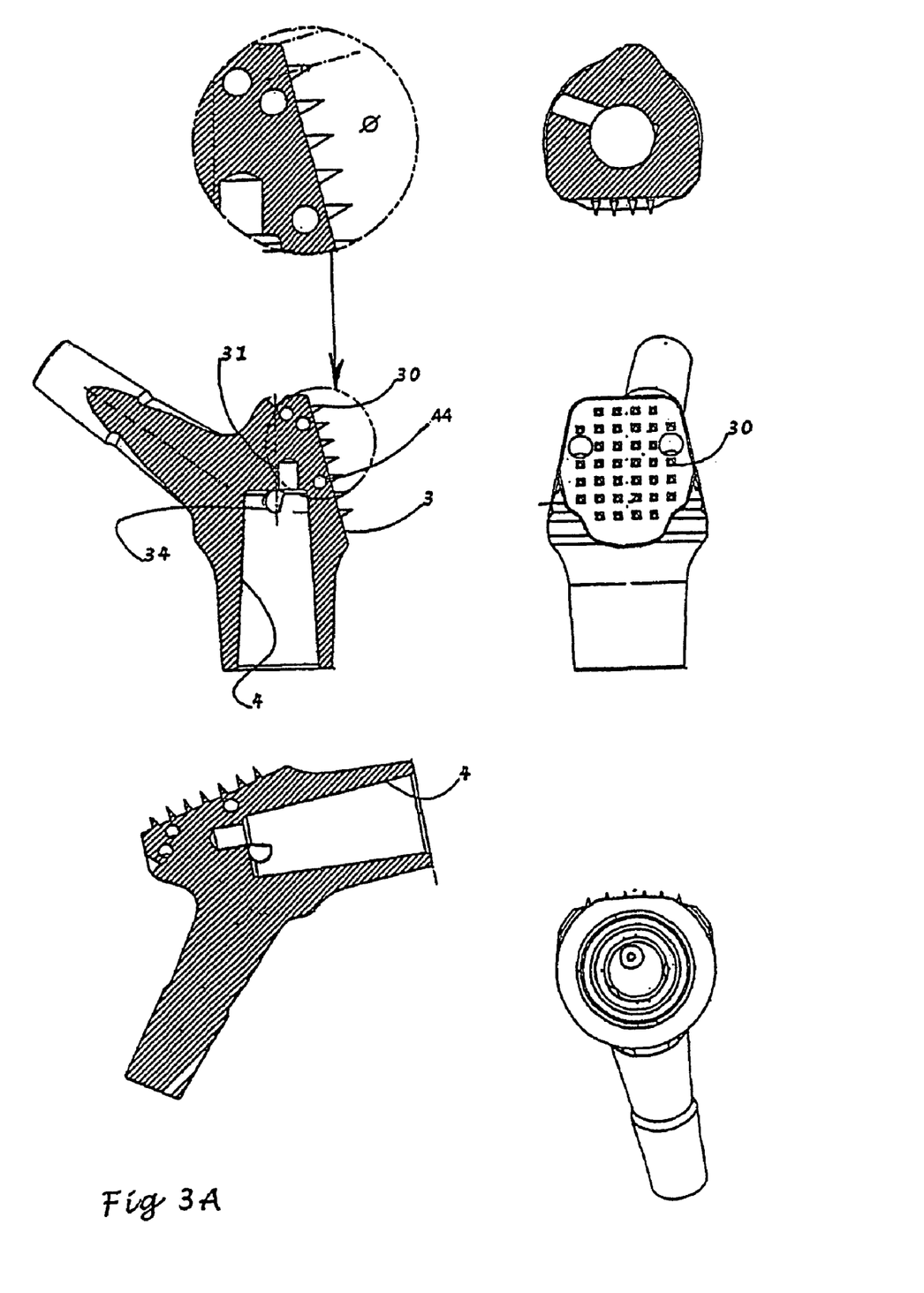
FIGS. 3A and 3B show various views of a trochanter replacement component in accordance with the invention.
Figure 3B:
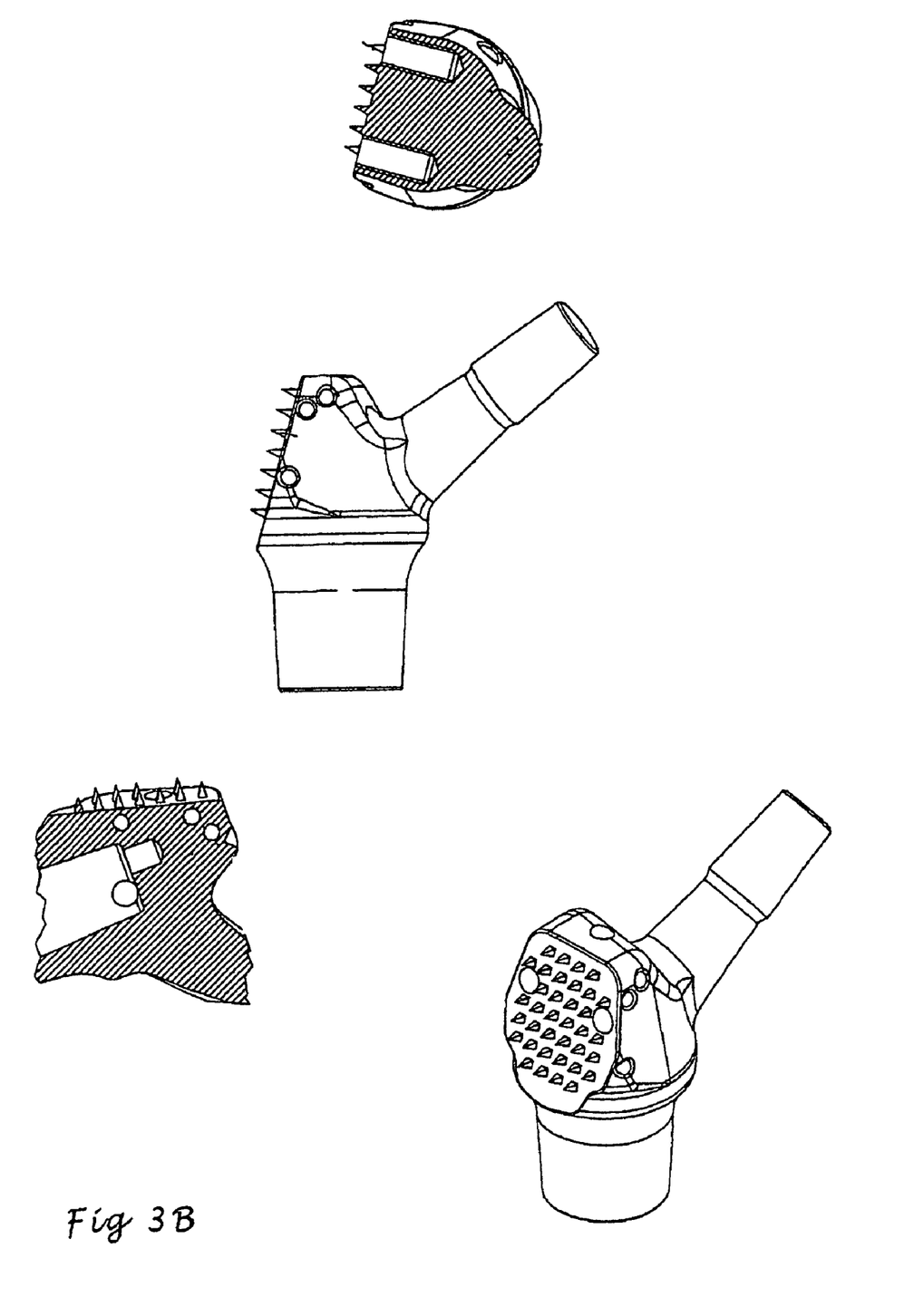
Figure 4A:
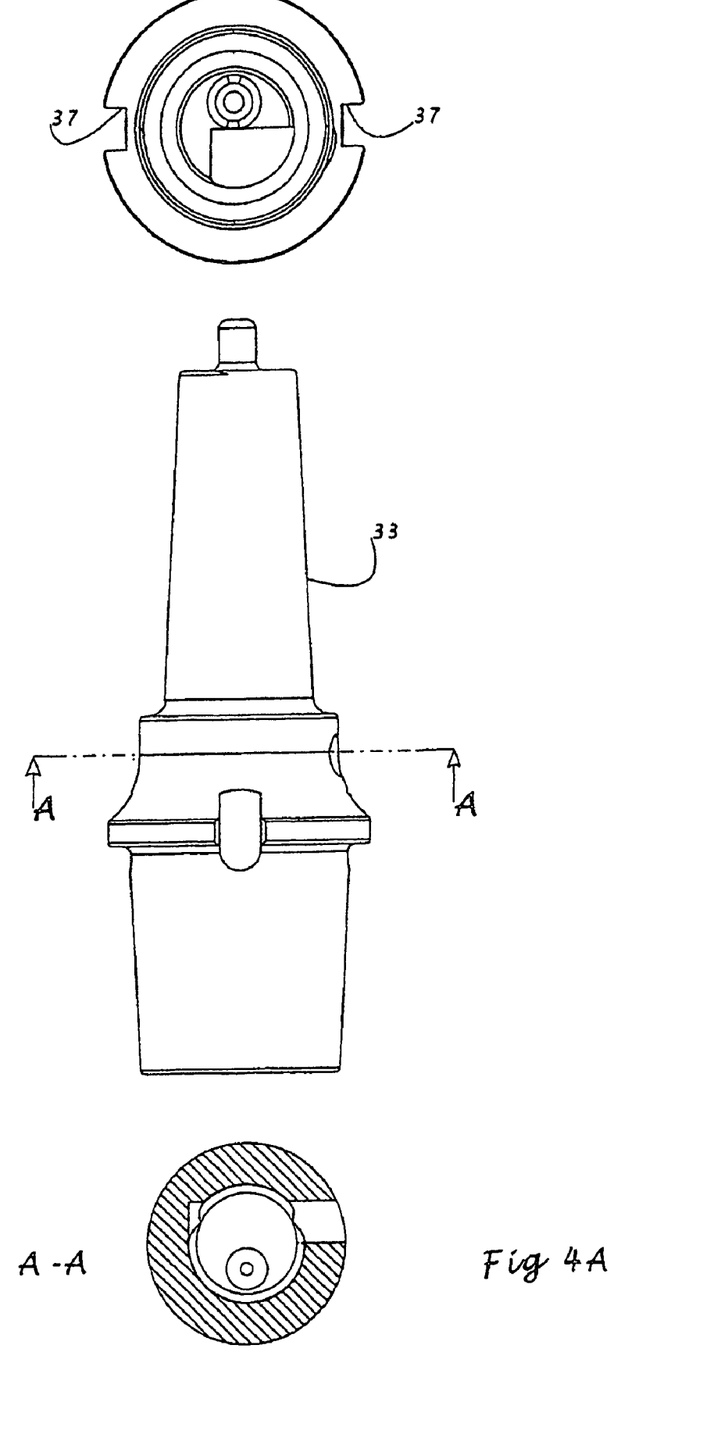
FIGS. 4A and 4B show various views of a modular shaft for use in the present invention.
Figure 4B:
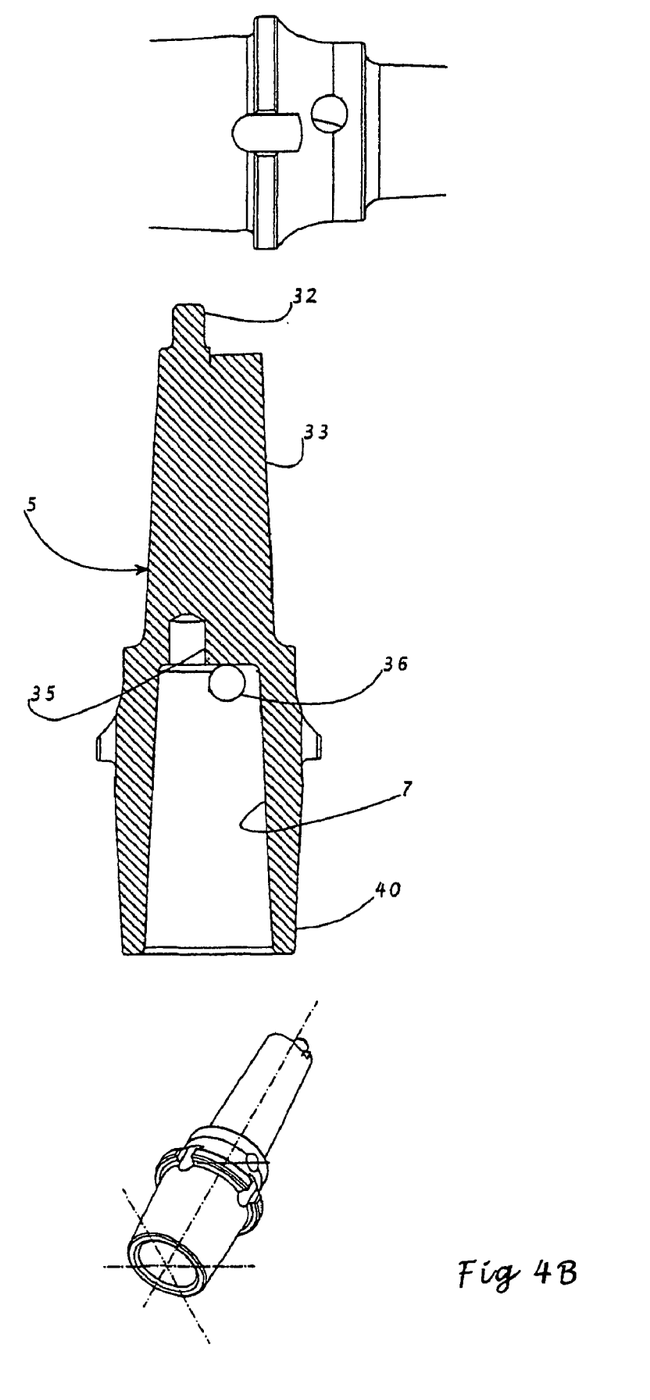

Details of the trochanter component 1 are shown in the views of FIG. 3. It would be seen that the flat face 3 of the trochanter component 1 are formed in a pattern of spikes 30. This pattern of spikes is provided to ensure a firm connection with any residual bone 12 (see FIG. 1) and serves to further stabilise the prosthesis. It would be seen that the trochanter component has a female taper terminating internally with an offset recess 31. Recess 31 is shaped to be engaged with a projection 32 formed on the male taper 33 of the shaft 5. (See FIG. 4). The trochanter component is provided with a transverse hole 34 into which a disassembly tool can be inserted to force the trochanter component and the shaft apart where disassembly is required. As can be seen in FIG. 4, the shaft 5 also has a female taper 7 and is formed with a similar recess 35 to the recess 31 in the trochanter component. Shaft 5 also includes a transverse hole 36 into which a disassembly tool can be inserted to force apart the shaft and the stem component which is designed to fit into the taper 7.

Referring further to FIG. 3, it will be seen that the trochanter component also incorporates holes 36. These are intended for suturing the trochanter component to soft tissue such as tendons in the event that there is no residual bone, to which tendons are attached, which could be clamped to the stippled face 3. The trochanter component is intended to be provided as a standard component of a modular system although there would be right and left handed versions. There may also be alternative trochanter components in which the degree of offset of the femoral neck differs to suit a particular patient.

As can be seen from FIG. 4, the femoral shaft, although standardised so far as the tapers are concerned, is supplied in lengths of 15 mm intervals. The femoral shaft is also provided with notches 37 designed to engage with corresponding lugs or ears 38 which are integral with the collar 10. The engagement of the collar on the shaft 5 and also the ears 38 in the notches 37 enables the collar to be fitted securely on the shaft. The lugs or ears 38 provide stability of the prosthesis against rotation. Suitably the collar has a pair of diametrically opposed ears 38 but in some embodiments may have only one such ear 38. Suitably the femoral shaft has more notches than the number of corresponding ears 38 and at a range of different spacings around the circumference to give the surgeon choice in the orientation of mounting of the collar, suitably at two different radial orientations spaced at 90 degrees to each other. This is particularly useful where the collar is ovoid cylindrical at its end face rather than circular cylindrical.

Figure 5:
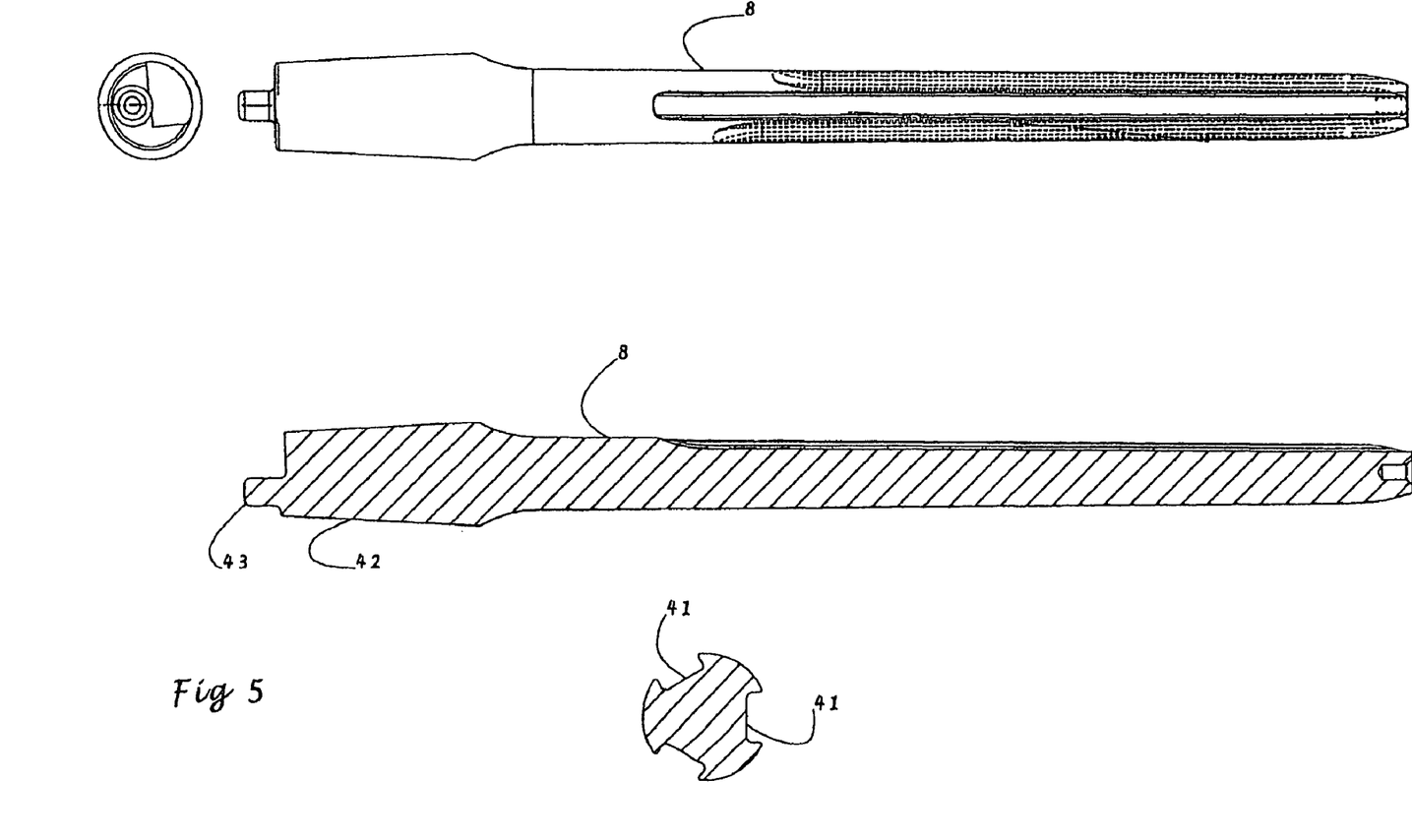
FIG. 5 shows various views of a femoral stem for use in the present invention.

FIG. 5 shows various views of the stem component 8. As can be seen from the cross-sectional view, the stem is formed with flutes for engaging in cortical bone and may be straight or curved to accommodate any curvature in the bone canal. The proximal end of the shaft has a taper 42 which corresponds with the internal taper 7 of the shaft component. The shaft also includes a projection 43 which corresponds with the recess 35 in the shaft component. The shaft component 5 includes a transverse hole 36 for disassembly purposes whereby a tool inserted through the hole will press apart the stem and the shaft by bearing on the corresponding end faces of the stem and shaft. As can be seen from FIG. 5, the stem is available in a number of diameters and lengths and may be curved or straight to accommodate the various surgical problems which might be encountered in fitting such a prosthesis.

Figure 6:
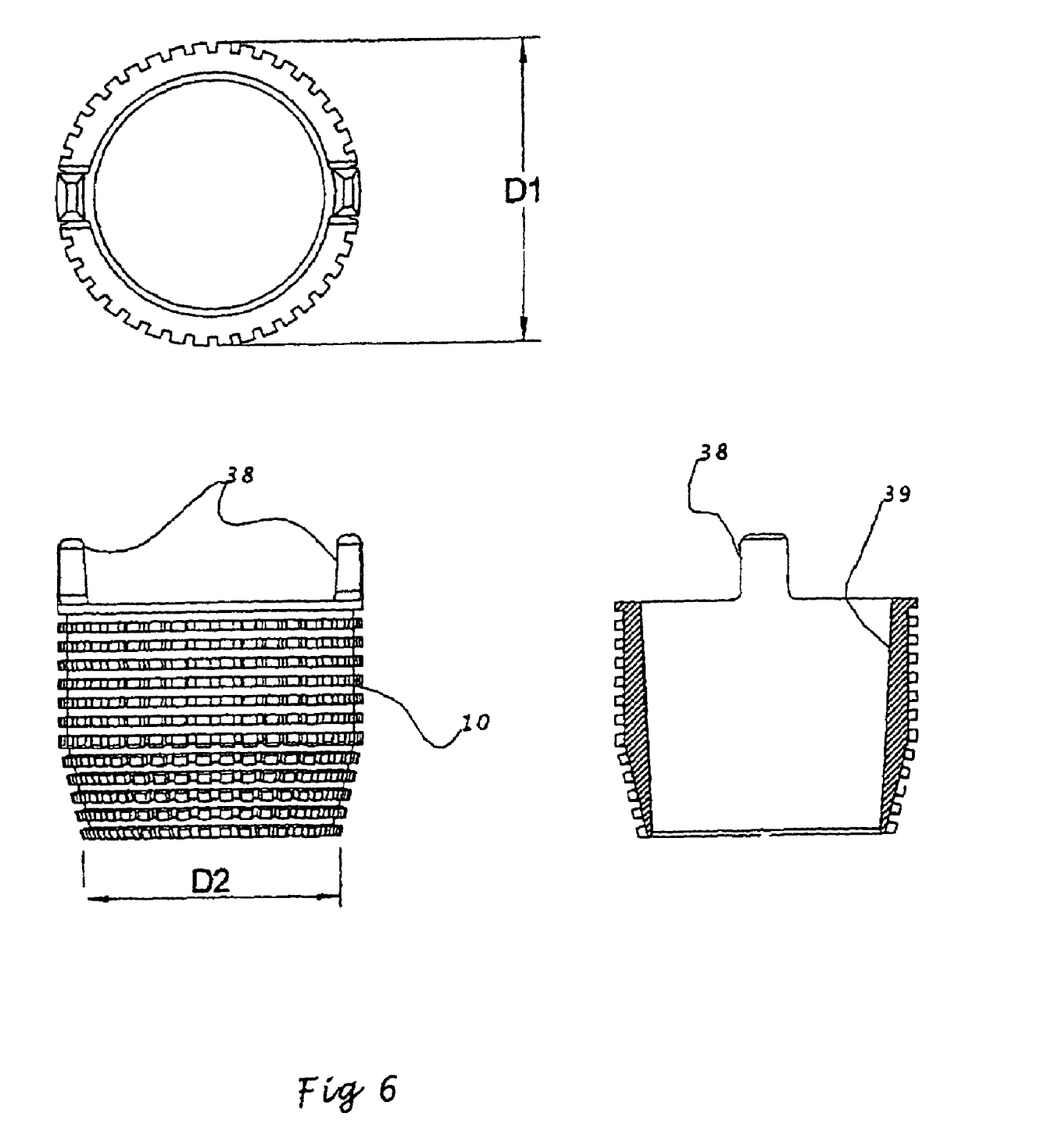
FIG. 6 shows various views of a collar for use in the prosthesis in accordance with the invention.
Figure 6B:
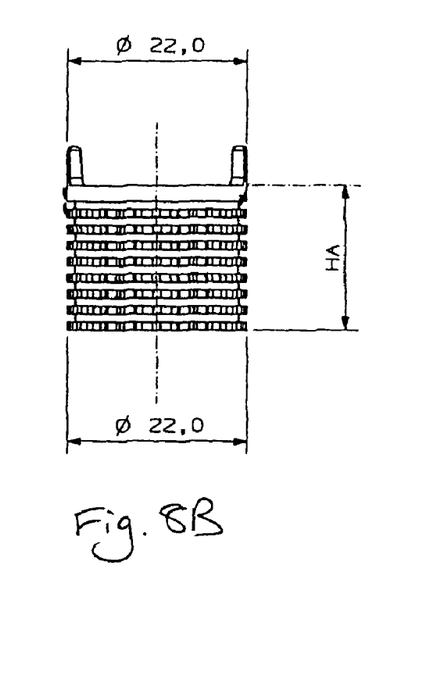
Figure 8A:
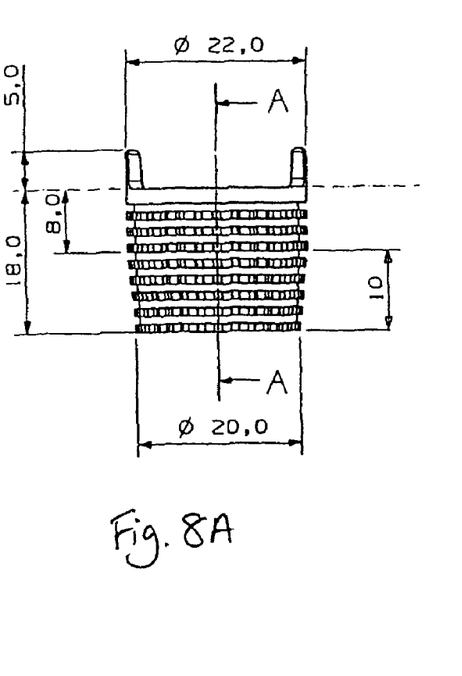
Figure 8C:
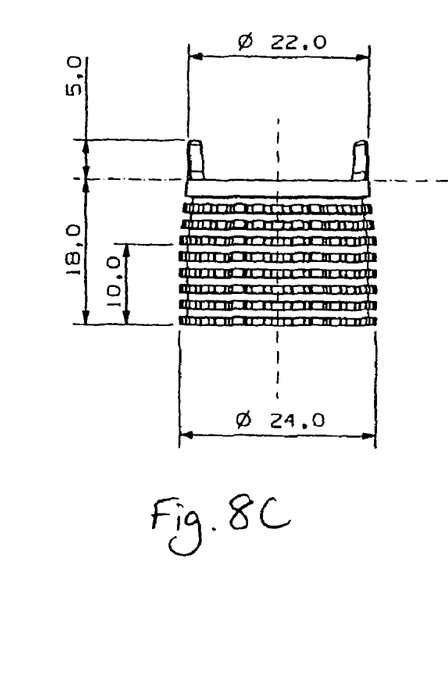
Figure 9:
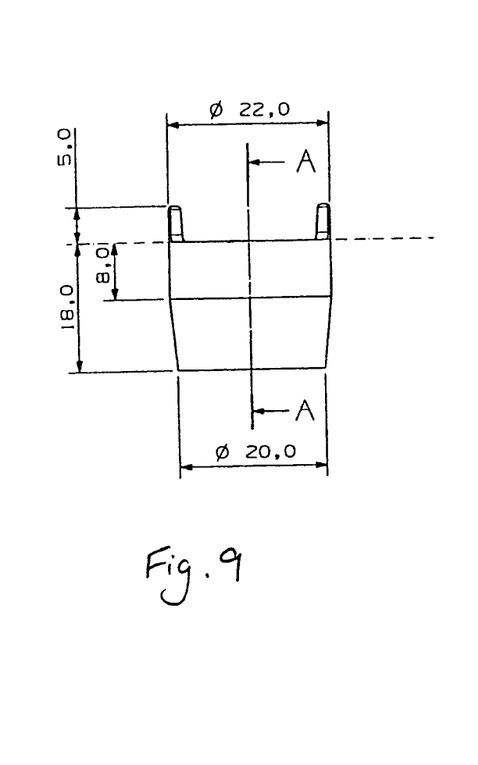
FIG. 9 is a side elevation view of a variant of collar without stippling being suitable for use in palliative limb reconstruction where there is no long term fixation requirement.
Figure 10A:
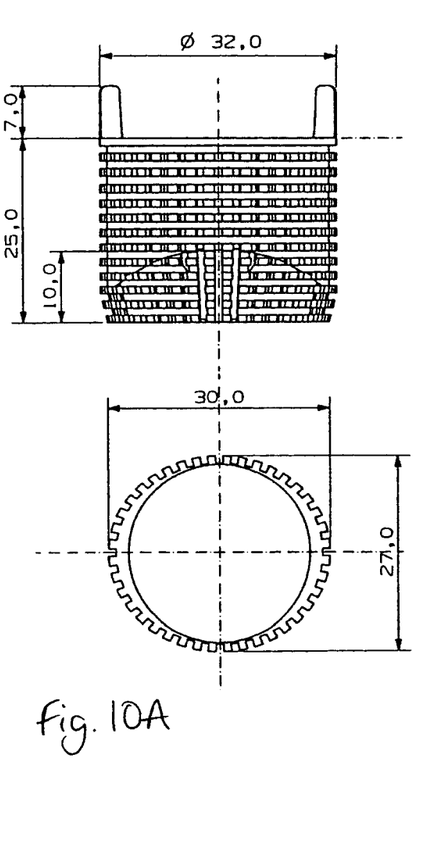
FIGS. 10A and 10B are side and distal end elevation views of two variants of the collar that are oval in end shape.
Figure 10B:
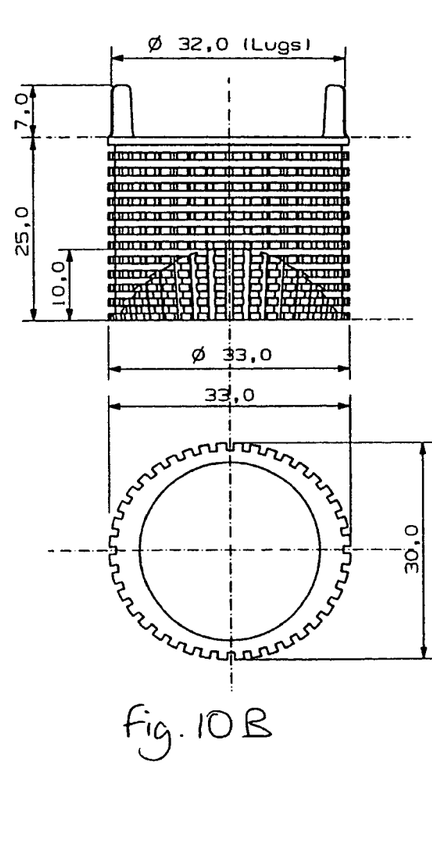
Figure 11A:
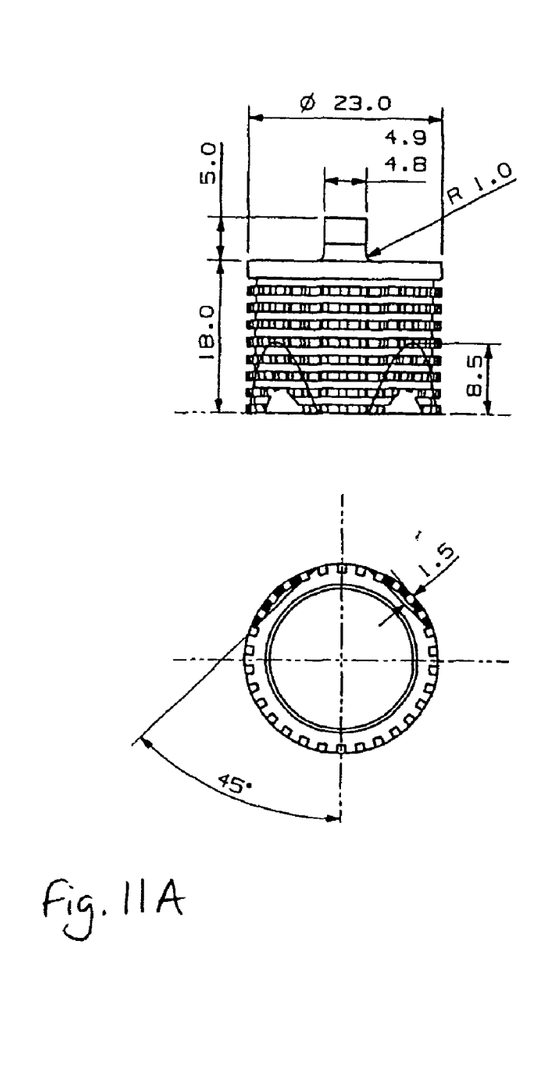
FIGS. 11A and 11B are side and distal end elevation views of two further variants of the collar that are roughly circular cylindrical in end shape but with flats to correspond to the resected bone end face.
Figure 11B:
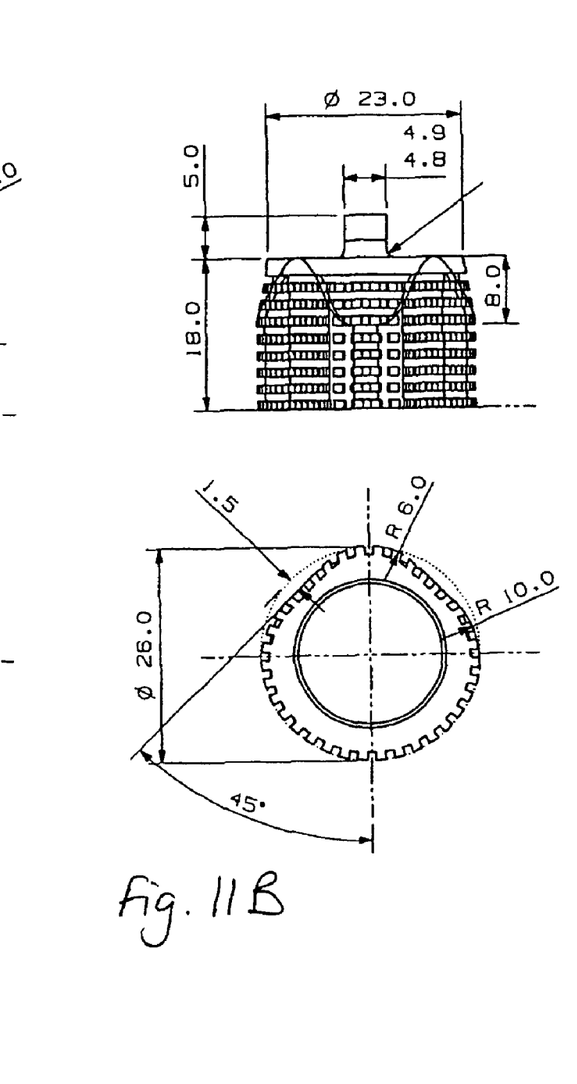

As can be seen from FIG. 6, collar 10 has an internal taper 39 adapted to fit on a corresponding taper 40 at one end of the shaft 5. As can be seen from FIGS. 6 and 8 to 11, the collar is supplied in a number of different forms, with different diameters, D1 and D2 as well as in a range of different shapes. The variants of the collar may be supplied individually or as a kit to enable the surgeon to select the best match in size and shape for the resected end face of the resected bone. In FIG. 6 the external cylindrical form of the collar is inwardly tapered towards the distal end facing toward the resected end face of the bone. The surface that is treated for osseointegration by stippling and hyrdoxyapatite (HA) coating is shown as extending over this tapered end portion and extending up the outer cylindrical surface too. In FIG. 8B the collar has no external taper and in FIG. 8C the collar is proximally tapered instead. In FIG. 9 a variant is shown having no stippling or HA coating and which is suitable for use in situations where no permanent fixation is required. In FIGS. 10A, 10B, 11A and 11B further variants are shown with ovoid or not wholly circular cylindrical distal or proximal ends.

Figure 7:
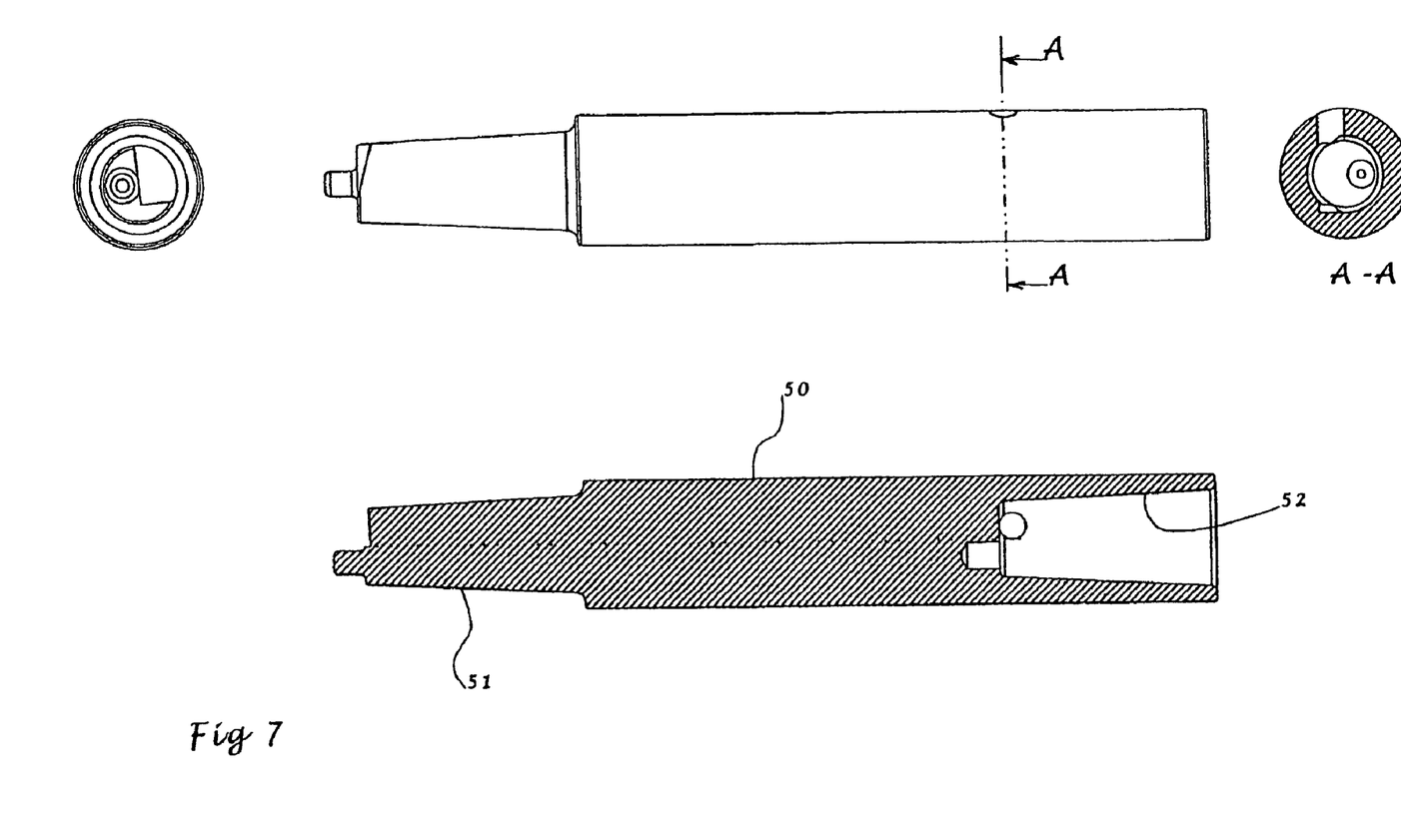
FIG. 7 shows several views of a modular extension shaft for use in the present invention.

FIG. 7 shows a modular extension shaft which enables the total assemblies as shown in FIGS. 1 and 2 to be extended. Modular extension shaft 50 has male and female tapes at opposite ends which correspond respectively with taper 7 of the modular shaft and taper 42 of the modular stem. Of course, modular extension shaft 50 may be used in conjunction with a standard shaft or alone to connect the trochanter component 1 or condular member 21 with the stems 8.

Although the prosthesis shown in FIGS. 1 and 2 is a femoral replacement prosthesis, analogously formed components could be employed to replace another long bone such as the humerus.

As described above, the components of the prosthesis can be readily dismantled by using a disassembly tool inserted in the transverse walls in the components at each tapered join either after a trial assembly or in a revision operation.

The material preferably used is a titanium alloy throughout except for the femoral heads where cobalt chromium or ceramic heads are preferably used.

The invention claimed is:

1. A prosthesis for partial replacement of a long bone in a patient, said prosthesis comprising:
   an end component forming one component of a prosthetic joint, said end component having a recess having an open end;
   a shaft having a shaft portion and a stem portion, said shaft portion being engageable with said end component and having a first end dimensioned and configured for receipt within said recess of said end component and said stem portion being engageable with the patient's long bone having a resected end face; and
   a collar having first and second opposing open ends and a throughbore extending between said open ends thereof, receivable over and mountable on said shaft, said collar being dimensioned and positionable on said shaft such that said second open end of said collar abuts the resected end face of the long bone, and wherein said second open end of said collar facing the resected end face of the long bone is sized and shaped to correspond to the size and shape of the resected end face of the long bone.

2. The prosthesis according to claim 1, wherein:
   said throughbore of said collar is substantially tubular shaped, and wherein the resected end face of the long bone has a peripheral edge and said collar has a peripheral edge defining said second open end of said collar which substantially corresponds to the size and shape of the peripheral edge of the resected end face of the long bone.

3. The prosthesis according to claim 1, wherein:
   the resected end face of the long bone has a peripheral edge and said collar has a peripheral edge defining said second open end of said collar, which is recessed relative to the peripheral edge of the resected end face of the long bone.

4. The prosthesis according to claim 1, wherein:
   at least a portion of said collar has a bone growth promoting surface treatment.

5. The prosthesis according to claim 1, wherein:
   at least a portion of said collar tapers towards the resected end face of the long bone.

6. The prosthesis according to claim 4, wherein:
   said portion of said collar is formed with an externally stippled surface.

7. The prosthesis according to claim 4, wherein:
   said portion of said collar is formed with an externally stippled surface and is coated with hydroxyapatite.

8. The prosthesis according to claim 1, wherein:
   said collar and said shaft have means for engagement.

9. The prosthesis according to claim 2, wherein:
   said collar has a circular cross-section.

10. The prosthesis according to claim 2, wherein:
    said collar has an ovoid cross-section.

11. The prosthesis according to claim 4, wherein:
    said portion of said collar is coated with hydroxyapatite.

12. The prosthesis according to claim 1, wherein:
    said throughbore of said collar is inwardly tapered, having a continuous taper between said first and second open ends of said collar and wherein said shaft is correspondingly outwardly tapered and complimentarily dimensioned for receipt within said throughbore of said collar.

13. The prosthesis according to claim 1, wherein:
    said shaft is releasably coupled to said end component.

14. The prosthesis according to claim 1, wherein:
    said collar is releasably coupled to said shaft.

15. The prosthesis according to claim 1, wherein:
said shaft is received within said collar via said first open end of said collar such that said collar can be slid over said shaft during assembly.

16. The prosthesis according to claim 1, wherein:
said shaft additionally comprises a shaft extension.

17. The prosthesis according to claim 8, wherein:
said means for engagement comprises a lug on said collar which is receivable within a corresponding recess on said shaft.

18. The prosthesis according to claim 1, wherein:
said shaft has an axial length which is dimensioned such that said second end of said collar abuts the resected end face of the long bone.

19. The prosthesis according to claim 1, wherein:
said end component is a trochanter replacement component.

20. The prosthesis according to claim 1, wherein:
said shaft portion is releasably coupled to said stem portion.

21. A kit for a prosthesis for partial replacement of a long bone in a patient, said prosthesis comprising:
an end component forming one component of a prosthetic joint, said end component having a recess having an open end;
a shaft having a shaft portion and at least one stem portion, said shaft portion being engageable with said end component and having a first end dimensioned and configured for receipt within said recess of said end component and said at least one stem portion being engageable with the patient's long bone having a resected end face; and
at least one collar having first and second opposing open ends and a throughbore extending between said open ends thereof, receivable over and mountable on said shaft, said collar being dimensioned and positionable on said shaft such that said second open end of said collar abuts the resected end face of the long bone.

22. The kit according to claim 21, wherein the kit comprises:
a greater number of collars than number of stems.

23. The kit according to claim 22, comprising:
only one stem and a plurality of differing collars.

24. The kit according to claim 23, comprising:
at least two substantially tubular shaped collars, one of which has an ovoid cross-section and the other of which has a circular cross-section.

25. The kit according to claim 23, comprising:
a plurality of collars, at least one of which is surface treated for osseo-integration.

26. The kit according to claim 21, wherein the kit comprises:
a plurality of collars having different diameters.

27. The kit according to claim 21, comprising:
a plurality of collars of different sizes.

28. The kit according to claim 21, comprising:
a plurality of collars of different shapes.

29. The kit according to claim 21, wherein:
said throughbore of said collar is substantially tubular shaped, and wherein the resected end face of the long bone has a peripheral edge and said collar has a peripheral edge defining said second open end of said collar which substantially corresponds to the size and shape of the peripheral edge of the resected end face of the long bone.

30. The kit according to claim 21, wherein:
the resected end face of the long bone has a peripheral edge and said collar has a peripheral edge defining said second open end of said collar, which is recessed relative to the peripheral edge of the resected end face of the long bone.

31. The kit according to claim 21, wherein:
at least a portion of said collar has a bone growth promoting surface treatment.

32. The kit according to claim 21, wherein:
at least a portion of said collar tapers towards the resected end face of the long bone.

33. The kit according to claim 31, wherein:
said portion of said collar is formed with an externally stippled surface.

34. The kit according to claim 31, wherein:
said portion of said collar is formed with an externally stippled surface and is coated with hydroxyapatite.

35. The kit according to claim 21, wherein:
said collar and said shaft have means for engagement.

36. The kit according to claim 29, wherein:
said collar has a circular cross-section.

37. The kit according to claim 29, wherein:
said collar has an ovoid cross-section.

38. The kit according to claim 31, wherein:
said portion of said collar is coated with hydroxyapatite.

39. The kit according to claim 21, wherein:
said throughbore of said collar is inwardly tapered, having a continuous taper between said first and second open ends of said collar and wherein said shaft is correspondingly outwardly tapered and complimentarily dimensioned for receipt within said throughbore of said collar.

40. The kit according to claim 21, wherein:
said shaft is releasably coupled to said end component.

41. The kit according to claim 21, wherein:
said collar is releasably coupled to said shaft.

42. The kit according to claim 21, wherein:
said shaft is received within said collar via said first open end of said collar such that said collar can be slid over said shaft during assembly.

43. The kit according to claim 21, wherein:
said shaft additionally comprises a shaft extension.

44. The kit according to claim 35, wherein:
said means for engagement comprises a lug on said collar which is receivable within a corresponding recess on said shaft.

45. The kit according to claim 21, wherein:
said shaft has an axial length which is dimensioned such that said second end of said collar abuts the resected end face of the long bone.

46. The kit according to claim 21, wherein:
said end component is a trochanter replacement component.

47. The kit according to claim 21, wherein:
said shaft portion is releasably coupled to said stem portion.

48. A prosthesis for partial replacement of a long bone in a patient, said prosthesis comprising:
an end component forming one component of a prosthetic joint, said end component having a recess having an open end;
a shaft having a shaft portion and a stem portion, said shaft portion being engageable with said end component and having a first end dimensioned and configured for receipt within said recess of said end component and said stem portion being engageable with the patient's long bone having a resected end face; and
a collar having first and second opposing open ends and a throughbore extending between said open ends thereof, receivable over and mountable on said shaft, said collar being dimensioned and positionable on said shaft such that said second open end of said collar abuts the resected end of face of the long bone.

49. The prosthesis according to claim 48, wherein:
said throughbore of said collar is substantially tubular shaped, and wherein the resected end face of the long bone has a peripheral edge and said collar has a peripheral edge defining said second open end of said collar which substantially corresponds to the size and shape of the peripheral edge of the resected end face of the long bone.

50. The prosthesis according to claim 48, wherein:
the resected end face of the long bone has a peripheral edge and said collar has a peripheral edge defining said second open end of said collar, which is recessed relative to the peripheral edge of the resected end face of the long bone.

51. The prosthesis according to claim 48, wherein:
at least a portion of said collar has a bone growth promoting surface treatment.

52. The prosthesis according to claim 48, wherein:
at least a portion of said collar tapers towards the resected end face of the long bone.

53. The prosthesis according to claim 51, wherein:
said portion of said collar is formed with an externally stippled surface.

54. The prosthesis according to claim 51, wherein:
said portion of said collar is formed with an externally stippled surface and is coated with hydroxyapatite.

55. The prosthesis according to claim 48, wherein:
said collar and said shaft have means for engagement.

56. The prosthesis according to claim 49, wherein:
said collar has a circular cross-section.

57. The prosthesis according to claim 49, wherein:
said collar has an ovoid cross-section.

58. The prosthesis according to claim 51, wherein:
said portion of said collar is coated with hydroxyapatite.

59. The prosthesis according to claim 48, wherein:
said throughbore of said collar is inwardly tapered, having a continuous taper between said first and second open ends of said collar and wherein said shaft is correspondingly outwardly tapered and complimentarily dimensioned for receipt within said throughbore of said collar.

60. The prosthesis according to claim 48, wherein:
said shaft is releasably coupled to said end component.

61. The prosthesis according to claim 48, wherein:
said collar is releasably coupled to said shaft.

62. The prosthesis according to claim 48, wherein:
said shaft is received within said collar via said first open end of said collar such that said collar can be slid over said shaft during assembly.

63. The prosthesis according to claim 48, wherein:
said shaft additionally comprises a shaft extension.

64. The prosthesis according to claim 55, wherein:
said means for engagement comprises a lug on said collar which is receivable within a corresponding recess on said shaft.

65. The prosthesis according to claim 48, wherein:
said shaft has an axial length which is dimensioned such that said second end of said collar abuts the resected end face of the long bone.

66. The prosthesis according to claim 48, wherein:
said end component is a trochanter replacement component.

67. The prosthesis according to claim 48, wherein:
said shaft portion is releasably coupled to said stem portion.

68. A method of installing a prosthesis for partial replacement of a long bone in a patient, comprising the steps of:
(i) providing a prosthesis having an end component forming one component of a prosthetic joint, said end component having a recess having an open end;
a shaft having a shaft portion and a stem portion, said shaft portion being engageable with said end component, said shaft portion having a first end dimensioned and configured for receipt within said recess of said end component and said stem portion being engageable with the patient's long bone having a resected end face; and
a collar having first and second opposing open ends and a throughbore extending between said open ends thereof;
(ii) resecting the patient's long bone so that it has a resected end face;
(iii) implanting said stem in said resected long bone;
(iv) engaging said shaft with said end component; and
(v) receiving said collar over and mounting on said shaft, said collar being dimensioned and positionable on said shaft such that said second open end of said collar abuts the resected end of face of the long bone.

* * * * *